(12) United States Patent
Kingsman et al.

(10) Patent No.: US 7,198,784 B2
(45) Date of Patent: *Apr. 3, 2007

(54) RETROVIRAL VECTORS

(75) Inventors: Alan John Kingsman, Oxford (GB); Susan Mary Kingsman, Oxford (GB); Narry Kim, Seoul (KR); Kyriacos Mitrophanous, Oxford (GB)

(73) Assignee: Oxford Biomedica (UK) Limited, Oxford (GB)

(*) Notice: Subject to any disclaimer, the term of this patent is extended or adjusted under 35 U.S.C. 154(b) by 121 days.

This patent is subject to a terminal disclaimer.

(21) Appl. No.: 10/661,761

(22) Filed: Sep. 11, 2003

(65) Prior Publication Data

US 2004/0086488 A1 May 6, 2004

Related U.S. Application Data

(60) Continuation-in-part of application No. 09/915,169, filed on Jul. 25, 2001, now Pat. No. 6,669,936, which is a division of application No. 09/224,014, filed on Dec. 28, 1998, now Pat. No. 6,312,682, which is a continuation of application No. PCT/GB97/02857, filed on Oct. 17, 1997.

(30) Foreign Application Priority Data

Oct. 17, 1996 (GB) ............................. 9621680.9
Nov. 25, 1996 (GB) ............................. 9624457.9

(51) Int. Cl.
*A61K 48/00* (2006.01)
*C12N 15/00* (2006.01)
*C12P 19/34* (2006.01)
*C07H 21/04* (2006.01)

(52) U.S. Cl. ................ 424/93.2; 435/320.1; 435/325; 435/91.33; 536/23.72

(58) Field of Classification Search ............ 435/320.1, 435/91.4, 325, 455; 424/93.2; 514/44
See application file for complete search history.

(56) References Cited

U.S. PATENT DOCUMENTS

| | | | |
|---|---|---|---|
| 5,554,524 A | | 9/1996 | Temin et al. |
| 5,585,263 A | * | 12/1996 | Hammarskj old et al. .. 435/236 |
| 5,665,577 A | | 9/1997 | Sodroski et al. |
| 5,739,118 A | * | 4/1998 | Carrano et al. ................ 514/44 |
| 5,981,505 A | | 11/1999 | Weiner |
| 5,994,136 A | | 11/1999 | Naldini |
| 6,013,516 A | * | 1/2000 | Verma et al. ................ 435/325 |
| 6,033,672 A | * | 3/2000 | Douvas et al. ........... 424/208.1 |
| 6,165,782 A | | 12/2000 | Naldini |
| 6,200,575 B1 | * | 3/2001 | Zagury et al. ........... 424/208.1 |
| 6,312,682 B1 | | 11/2001 | Kingsman |
| 6,326,007 B1 | | 12/2001 | Yilma |
| 6,428,953 B1 | | 8/2002 | Naldini |
| 6,468,539 B1 | * | 10/2002 | Cohen et al. ............. 424/192.1 |

FOREIGN PATENT DOCUMENTS

| | | |
|---|---|---|
| EP | 0 213 894 | 8/1986 |
| EP | 0611822 | 8/1994 |
| EP | 0759471 | 2/1997 |
| WO | WO 91/19798 | 12/1991 |
| WO | WO 92/21750 | 12/1992 |
| WO | WO95/30755 | 11/1995 |
| WO | WO 97/12622 | 4/1997 |
| WO | WO 97/14809 | 4/1997 |
| WO | WO97/14809 | 4/1997 |

OTHER PUBLICATIONS

Harmache et al (J. Virol. 69(9): 5445-5454, 1995).*
Bray et al (Proc. Nat. Acad. Sci. USA 91: 1256-1260, 1994).*
Coffin et al (in Retroviruses Cold Spring Harbor Laboratory Press, 1997, p. 58).*
Chang et al (Virology 211: 157-169, 1995).*
Luznik (J. Clin. Invest. 95: 328-332, 1995).*
Kestler et al, "Importance of th enef Gene for Maintenance of High Virus Loads and for Development of AIDS", Cell 65:651-662 (1991).
Blomer et al., "Highly Efficient and Sustained Gene Transfer in Adult Neurons with a Lentivirus Vector", Journal of Virology 97, 1997, p. 6641-6649.
Blomer et al., "Applications of gene therapy to the CNS", Human Molecular Genetics 5, 1996, p. 1397-1404.
Clever et al., RNA Secondary Structure and Binding Sites for gag Gene Products in the 5' Packaging Signal of Human Immundeficiency Virus Type 1, Journal of Virology 69, 1995, p. 2101-2109.
Clever et al., "Mutant Human Immunodeficiency Virus Type 1 Genomes with Defects in RNA Dimerization or Encapsidation", Journal of Virology 71, 1997, p. 3407-3414.
John M. Coffin, "Retroviridae: The Virsuses and Their Replication", Fields of Virology 3, 1996, p. 1767-1996.
Fuller et al., "Vesicular Stomatitis Virus Infects and Matures Only through the Basolateral Surface of the Polarized Epithelial Cell Line, MDCK", Cell 38, 1984, p. 65-77, p. 65-77.
Harrison et al., "Inhibition of HIV Production in Cells Containing an Integrated, HIV-Regulated Diphtheria Toxin A Chain Gene", Aids Research and Human Retroviruses 8, 1992, p. 39-45.
Hayashi et al., "RNA Packaging Signal of Human Immunodeficiency Virus Type 1", Virology 188, 1992, p. 590-599.
Kim et al., "Minimal Requirement for a Lentivirus Vector Based on Human Immunodeficiency Virus Type 1", Journal of Virology 72, 1998, p. 811-816.

(Continued)

*Primary Examiner*—Richard Schnizer
(74) *Attorney, Agent, or Firm*—Frommer Lawrence & Haug LLP; Thomas J. Kowalski; Anne-Marie C. Yvon (57) ABSTRACT

Retroviral vector production systems for producing lentivirus-based vector particles which are capable of infecting and transducing non-dividing target cells, wherein one or more of the auxiliary genes such as vpr, vif, tat, and nef in the case of HIV-1 are absent from the system. The systems and resulting retrovirus vector particles have improved safety over existing systems and vectors.

19 Claims, 3 Drawing Sheets

OTHER PUBLICATIONS

Kim et al., "Temporal Aspects of DNA and RNA Synthesis during Human Immunodeficiency Virus Infection: Evidence for Differential Gene Expression", Journal of Virology 63, 1989, p. 3708-3713.
Mann et al., "Construction of a Retrovirus Packaging Mutant and Its Use to Produce Helper Free Defective Retroviruses", Cell, vol. 33, 1983, p. 153-159.
Martarano et al., "Equine Infectious Anemia Virus trans-Regulatory Protein Rev Controls Viral mRNA Stability, Accumulation, and Alternative Splicing", Journal of Virology 68, 1994, p. 3102-3111.
Payne et al., "Characterization of infectious molecular clones of equine infectious anaemia virus", Journal of General Virology 75, 1994, p. 425-429.
Yee et al., "A general method for the generation of high-titer, pantropic retroviral vectors: Highly efficient infection of primary hepatocytes", Proc. Natl. Acad. Sci. USA 91, 1994, p. 9564-9568.
Carroll et al., "*E. coli* beta-Glucuronidase (GUS) as a Marker for Recombinant Vaccinia Viruses", BioTechniques 19, 1995, p. 352-354.
Carroll et al., "Host Range and Cytopathogenicity of the Highly Attenuated MVA Strain of Vaccinia Virus: Propagation and Generation of Recombinant Viruses in a Nonhuman Mammalian Cell Line", Virology 238, 1997, p. 198-211.
Chakrabarti et al., "Vaccinia Viruse expression Vector: Coexpression of beta-Galactosidase Provides Visual Screening of Recombinant Virus Plaques", Molecular and Cellular Biology, 5, 1985, p. 3403-3409.
Chakrabarti et al., "Compact, Synthetic, Vaccinia Virus Early/Late Promoter for Protein Expression", BioTechniques 23, 1997, p. 1094-1097.
Davison et al., "Structure of Vaccinia Virus Early Promoters", J. Mol. Biol. 210, 1989, p. 749-769.
Davison et al. "Structure of Vaccinia Virus Late Promoters", J. Mol. Biol. 210, 1980, p. 771-784.
Earl et al., "Preparation of Cell Cultures and Vaccinia Virus Stocks", Current Protocols in Molecular Biology 1998, Suppl. 43 Unit 16.16.
Earl et al., "Generation of Recombinant Vaccinia Viruses", Current Protocols in Molecular Biology 1998, Suppl. 43 Unit 16.17.
Flexner et al. "Prevention of vaccinia virus infection in immunodeficient mice by vector-directed IL-2 expression", Nature 330, 1987, p. 259-262.
Holzer et al., "Construction of a Vaccinia Virus Deficient in the Essential DNA Repair Enzyme Uracil DNA Glycosylase by a Complementing Cell Line", Journal of Virology 71, 1997, p. 4997-5002.
Mackett et al., "Vaccinia virus: A selectable eukaryotic cloning and expression vector", Proc. Natl. Acad. Sci. USA 79, 1982, p. 7415-7419.
Mahnel et al., "Erfahrungen bei der Schutzimpfung gegen Orthopocken von Mensch und Tier mit dem Impstamm MVA", English translation, Berl und Munchener Tierartzliche Wochenschrift 107, 1994, p. 253-256.
Mayr et al., "The Smallpox Vaccination Strain MVA: Marker, Genetic Structure, Experience Gained with the Parenteral Vaccination and Behavior in Organisms with a Debilitated Defence Mechansism", Zentralbl. Bakteriol, 1978, p. 375-390 (English Abstract).
Meyer et al., "Mapping of deletions in the genome of the highly attenuated vaccinia virus MVA and their influence on virulence", Journal of General Virology 72, 1991, p. 1031-1038.
Bernard Moss, "Poxviridae: The Viruses and Their Replication", Fields Virology 3, 1996, p. 2637-2672.
Moss et al., "Host Range Restricted Non-Replicating Vaccinia Virus Vectors as Vaccine Candidates", Adv Exp Med Biol 367, 1996, p. 7-13.
Panicali et al., "Construction of poxviruses as cloning vectors: Insertion of the thymidine kinase gene from herpes simplex virus into the DNA of infectious vaccinia virus", Proc. Natl. Acad. Sci. USA, 79, 1982, p. 4927-4931.
Soneoka et al., "A transient three-plasmid expression system for the production of high titer retroviral vectors", Necleic Acids Research, vol. 23, 1995, p. 628-633.
Sutter et al., "Nonreplicating vaccinia vector efficiently expresses recombinant genes", Proc. Natl. Acad. Sci. USA, 1992, p. 10847-10851.
Taylor et al., "Nonreplicating Viral Vectors as Potential Vaccines: Recombinant Canarypox Virus Expressing Measles Virus Fusion (F) and Hemagglutinin (HA) Glycoproteins", Virology 187, 1992, p. 321-328.
Paoletti et al., "Safe and Effective Poxvirus Vectors-NYVAC and ALVAC", Dev Biol Stand 82, 1994, p. 65-69.
Wyatt et al., "Replication-Deficient Vaccinia Virus Encoding Bacteriophage T7 RNA Polymerase for Transient Gene Expression in Mammalian Cells", Virology 210, 1995, p. 202-205.
Wyatt et al., "Marker Rescue of the Host Range Restriction Defects of Modified Vaccinia Virus Ankara", Virology 251, 1998, p. 334-342.
Wyatt et al., "Development of a replicaiton-deficient recombinant vaccinia virus vaccine effective against parainfluenza virus 3 infection in an animal model", Vaccine 14, 1996, p. 1451-1458.
W. French Anderson. Human gene therapy. Nature. vol. 392, pp. 25-30, 1998.
Verma et al. Gene therapy-promises, problems and prospects. Nature. vol. 389, pp. 239-242, 1997.
L. Naldini et al., "In vivo Gene Delivery and Stable Transduction of Nondividing cells by a Lentiviral Vector", Science, vol. 272, Apr. 12, 1996, pp. 263-267, XP000583652.
Zufferey et al., "Multiply attenuated lentiviral vector achieves efficient gene delivery in vivo", Nature Biotechnology vol. 15, Sep. 1997, pp. 871-875, XP-002056816.
Akkina et al. "High-Efficiency Gene Transfer into CD34.sup.+ Cells with a Human Immunodeficiency Virus Type 1-Based Retroviral Vector Pseudotyped with Vesicular Stomatitis Virus Envelope Glycoprotein G", Journal of Virology, Apr. 1996, pp. 2581-2585.
Barillari et al., "The Tat protein of human immunodeficiency virus type 1, a growth factor for AIDS *Kaposi sarcoma* and cytokine-activated vascular cells, induces adhesion of the same cell types by using integrin receptors recognizing the RGD amino sequence", Proc. Natl. Acad. Sci. USA, vol. 90, Sep. 1993, pp. 7941-7945.
Buchschacher, Jr. et al., "Human Immunodeficiency Virus Vectors for Inducible Expression of Foreign Genes", Journal of Virology, May 1992, pp. 2731-2739.
Bukrinsky et al., "A nuclear localization signal within HIV-1 matrix protein that governs infection of non-dividing cells", Nature, vol. 365, Oct. 14, 1993, pp. 666-669.
Cannon et al., "Murine Leukemia Virus-Based Tat-Inducible Long Terminal Repeat Replacement Vectors: a New System for Anti-Human Immunodeficiency Virus Gene Therapy", Journal of Virology, Nov. 1996, pp. 8234-8240.
Chen et al., "High-Efficiency Transformation of Mammalian Cells by Plasmid DNA", Molecular and Cellular Biology, Aug. 1987, p. 2745-2752.
Echetebu et al., "Construction and Characterization of a Potent HIV-2 Tat Transdominant Mutant Protein", Journal of Acquired Immune Deficiency Syndromes, 1994 Raven Press, Ltd., New York, pp. 655-664.
Ensoli et al., "Tat protein of HIV-1 stimulates growth of cells derived from Kaposi's sarcoma lesions of AIDS patients", Nature, vol. 345, May 3, 1990, pp. 84-87.
Gallay et al., "Role of the Karyopherin Pathway in Human Immunodeficiency Virus Type 1 Nuclear Import", Journal of Virology, Feb. 1996, pp. 1027-1032.
Heinzinger et al., "The Vpr protein of human immunodeficiency virus type 1 influences neclear localization of viral nucleic acids in nondividing host cells", Proc. Natl. Acad. Sci. USA, vol. 91, Jul. 1994, pp. 7311-7315.
Jong et al., "Lentiviruses", Fields Virology, Third Edition, 1996, chapter 62, pp. 1977-1996.
Jowett et al., "The Human Immunodeficiency Virus Type 1 vpr Gene Arrestes Infected T Cells in the G.sub.2 + M Phase of the Cell Cycle", Journal of Virology, Oct. 1995, pp. 6304-6313.
Sunyoung Kim et al., "Temporal Aspects of DNA and RNA Synthesis during Human Immunodeficiency Virus Infection: Evidence for Differential Gene Expression", Journal of Virology, Sep. 1989, pp. 3708-3713.

Lever et al., "Identification of a Sequence Required for Efficient Packaging of Human Immunodeficiency Virus Type 1 RNA into Virions", Journal of Virology, Sep. 1989, pp. 4085-4087.

Levy et al., "Induction of Cell Differentiation by Human Immunodeficiency Virus 1 vpr", Cell, vol. 72, Feb. 26, 1993 pp. 541-550.

Cell, vol. 72, Feb. 26, 1993 pp. 1245-1252.

Levy et al., "Extracellular Vpr Protein Increases Cellular Permissiveness to Human Immunodeficiency Virus Replication and Reactivates Virus from Latency", Journal of Virology, vol. 69, Feb. 1995, pp. 1243-1252.

Lisziewicz et al., "Inhibition of human immunodeficiency virus type 1 replication by regulated expression of a polymeric Tat activation response RNA decoy as a strategy for gene therapy in AIDS", Proc. Natl. Acad. Sci. USA, vol. 90, Sep. 1993, pp. 8000-8004.

Mahalingham et al., "Functional Analysis of HIV-1 Vpr: Identification of Determinants Essential for Subcellular Localization", Virology 212, 1995, pp. 331-339.

Naldini et al., "In Vivo Gene Delivery and Stable Transduction of Nondividing Cells by a Lentiviral Vector", Science, vol. 272, Apr. 12, 1996, pp. 263-267.

Naldini et al., Efficient transfer, integration, and sustained long-term expression of the transgene in adult rat brains injected with a lentiviral vector, Proc. Natl. Acad. Sci. USA, vol. 93, Oct. 1996, pp. 11382-11388.

Page et al., "Construction and Use of a Human Immunodeficiency Virus Vectro for Analysis of Virus Infectivitiy", Journal of Virology, vol. 64, No. 1, Nov. 1990, pp. 5270-5276.

Poznansky et al., "Gene Transfer into Human Lymphocytes by a Defective Human Immunodeficiency Virus Type 1 Vector", Journal of Virology, vol. 65, No. 1, Jan. 1991, pp. 531-536.

Richardson et al., "Helper virus free transfer of human immunodeficiency virus type 1 vectors", Journal of General Virology, vol. 76, 1995, pp. 691-696.

Ross et al., "Gene Therapy in the United States: A Five-Year Status Report", Human Gene Therapy 7, vol. 77, Sep. 10, 1996, pp. 1781-1790.

Shimada et al., "Targeted and Highly Efficient Gene Transfer into CD4.sup.+ Cells by a Recombinant Human Immunodeficiency Virus Retroviral Vector", The Journal of Clinical Investigation, Inc., vol. 88, Sep. 1991, 1043-1047.

Tomonaga et al., "Molecular biology of the feline immunodeficiency virus auxiliary genes", Journal of General Virology, 1996, pp. 1611-1621.

Lewis et al Fred Hutchinson Cancer Research, "Passage through Mitosis Is Required for Oncoretroviruses but Not for the Human Immunodeficiency Virus", Journal of Virology, vol. 68, No. 1, Jan. 1994, pp. 510-516.

Buchschacher et al., "Human Immunodeficiency Virus Vectors for Inducible Expression of Foreign Genes", Journal of Virology, vol. 66, No. 5, May 1992, pp. 2731-2739.

Naldini et al., "In Vivo Gene Delivery and Stable Transduchtion of Nondividing Cells by a Lentiviral Vector", Science, vol. 272, Apr. 12, 1996.

R G Vile et al., "Retroviruses as vectors", British Medical Bulletin, 1995, vol. 51, pp. 12-30.

Bowtell et al., "Comparison of Expression in Hemopoietic Cells by Retroviral Vectors Carrying Two Genes", Journal of Virology, Jul. 1988, pp. 2464-2473.

Correll et al., "Retroviral Vector Design for Long-Term Expression in Murine Hematopoietic Cells In Vivo", Blood, vol. 84, No. 6, Sep. 15, 1994, pp. 1812-1822.

Emerman et al., "Genes with Promoters in Retrovirus Vectors Can Be Independently Suppressed by an Epigenentic Mechanism", Cell, vol. 39, Dec. 1984, pp. 458-467.

Ghattas et al., "The Encephalomyocarditis Virus Internal Ribosome Entry Site Allows Efficient Coexpression of Two Genes from a Recombinant Provirus in Cultered Cells and in Embryos", Molecular and Cellular Biology, Dec. 1991, pp. 5848-5859. vol. 11 No. 12.

Hantzopoulos et al., "Improved gene expression upon transfer of the adenosine deaminase minigene outside the transcriptional unit of a retroviral vector", Proc. Natl. Acad. Sci. USA, vol. 86, May 1989, pp. 3519-3523.

Hatzoglou et al., "Hormonal Control of Interacting Promoters Introduced into Cells by Retroviruses", The Journal of Biological Chemistry, vol. 266, issue of May 5, 1991, pp. 6416-6425.

Hatzoglou et al., "Hormonal Regulation of Chimeric Genes Containing the Phospphoenolpyruvate Carboxykinase Promoter Regulatory Region in Hepatoma Cells Infected by Murine Retroviruses", The Journal of Biological Chemistry, vol. 268, No. 33, No. 26, 1988, pp. 17798-17808.

Hantzopoulos et al., "Comparison of the Expression of a Mutant Dihydofolate Reductase under Control of Different Internal Promoters in Retroviral Vectors", Human Gene Therapy, 1992, pp. 381-390.

McLachlin et al., "Factors Affecting Retroviral Vector Function and Structural Integrity", Virology 195, 1993, pp. 1-5.

Overall et al., "Stably Transmitted Triple-Promoter Retroviral Vectors and Their Use in Transformation of Primary Mammalian Cells", Molecular and Cellular Biology, Apr. 1988, pp. 1803-1808.

Scharfmann et al., "Long-term in vivo expression of retrovirus-mediated gene transfer in mouse fibroblast implants", Proc. Natl. Acad. Sci. USA, vol. 88, Jun. 1991, pp. 4626-4630.

Vile et al., "A comparison of the properties of different retroviral vectors containing containing the murine tyrosinase promoter to achieve transcriptionally targeted expression of the HSVtk or IL--2 genes", Gene Therapy, 1994, pp. 307-316.

Lixu et al., "Factors Affecting Long-Term Stability of Moloney Murine Leukemia Virus-Based Vectors", Virology vol. 171, 1989, pp. 331-341.

Jiing-Kuan Yee et al., "Gene expression from transcriptionally disabled retroviral vectors", Proc. Natl. Acad. Sci. USA, vol. 84, Aug. 1987, pp. 5197-5201.

Bryan R. Cullen, "Regulation of HIV gene expression", AIDS. vol. 6 1995, pp. S19-S32.

Ngo et al., in The Protein Folding problem and tertiary Structure prediction, merz et al., 9ed.), Birkhauser, Boston, MA pp. 492-495, 1994.

Tabernero et al. "The Posttranscriptional Control Element of the Simian Retrovirus Type 1 Forms an Extensive RNA Secondary Structure Necessary for Its Function" Journal of Virology, Sep. 1996, pp. 5998-6011.

Zolotukhin et al. "Rev of human immunodeficiency virus and Rex of the human T-cell leukemia virus type I can counteract an mRNA downregulatory element of the transferrin receptor mRNA" Nucleic Acids Res 1994, Nov. 11, 22(22): 4725-32.

Rimsky et al. "Functional replacement of the HIV-1 rev protein by the HTLV-1 rex protein" Nature Oct. 20, 1988: 335 (6192) 738-40.

Zolotukhin et al. "Continuous Propagation of RRE(-) and Rev(-) Human Immunodeficiency Virus Type I Molecular Clones Containing a cis-acting element of Simian Retrovirus Type 1 in Human Peripheral Blood Lymphocytes" J Virol Dec. 1994 68(12): 7944-52.

Bray et al. A small element from the Mason-Pfizer monkey virus genome makes human-immunodeficieny virus type 1 expression and replication Rev-independent (1994) Proc. Natl. Acad. Sci. 91: 1256-1260.

Harmache, et al. The Caprine Arthritis Encephalitis Virus tat Gene is Dispensable for Efficient Viral Replication in Vitro and in Vivo (1995) Journal of Virology, Sep. 1995, p. 5445-5454.

Phillips, et al. Identification of the Rev Transactivation and Rev-Responsive Elements of Feline Immunodeficiency Virus (1992) Journal of Virology, Sep. 1992, p. 5464-5471.

Shibata, et al. Construction and Characterization of an Infectious DNA Clone and Mutants of Simian Immunodeficiency Virus Isolated from the African Green Monkey (1990) Journal of Virology, Jan. 1990, p. 307-312.

Sakai, H. et al. Compatibility of rev Gene Activity in the Four Groups of Primate Lentiviruses, (1990) Journal of Virology, 184: 513-520.

Sakai, H. et al. Archives of Virology, Compatibility of Tat and Rev Transactivators Groups of Primate Lentiviruses, (1993) Archives of Virology 129: 1-10.

Shibata, R. et al. Archives of Virology, Comparative Studies on tat Mutants of Three Primate Lentiviruses, (1990) 114: 243-250.

Shibata, R. et al. Journal of Medical Primatology, Mutational Analysis of Simian Immunodeficiency Virus From African Green Monkeys and Human Immuno-deficiency Virus Type 2 (1990), 19: 217-225.

Adachi A. et al. Archives of Virology, Generation and characterization of the human immunodeficiency virus type 1 mutants, (1991) 117: 45-48.

Gibbs, J.S., et al. Construction and In Vitro Properties of HIV-1 Mutants with Deletions in "Nonessential" Genes, (1994) 10(4): 343-340, Aids Res. Hum. Retrovir.

Gibbs, J.S., et al. AIDS Research and Human Retroviruses, Construction and In Vitro Properties of SIV mac Mutants with Deletions in "Nonessential" Genes, (1994) 10(5): 607-616, Aids Res. Hum. Retrovir.

Nishino, Y. et al. Archives of Virology Human Immunodeficiency Virus Type 1vif, vpr, and vpu Mutants Can Produce Persistently Infected Cells, (1991) 120: 181-192.

Cho, S. et al. (1995) AIDS Research and Human Retroviruses, Replication of HIV Type 1 in Rabbit Cell Lines is Not Limited by Deficiencies in tat, rev, or Long Terminal Repeat Function, (1995) 11(12): 1487-1493.

* cited by examiner

SEQUENCE LISTING

```
<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: oligonucleotide

<400> SEQUENCE: 1
cgtgaattcg cctaaaactg cttgtacca                              29

<210> SEQ ID NO 2
<211> LENGTH: 21
<212> TYPE: DNA
<213> ORGANISM: Artificial Sequence
<220> FEATURE:
<223> OTHER INFORMATION: oligonucleotide

<400> SEQUENCE: 2
gaactaatga ccccgtaatt g                                      21

<210> SEQ ID NO 3
<211> LENGTH: 38
<212> TYPE: DNA
<213> ORGANISM: Artificial Sequence
<220> FEATURE:
<223> OTHER INFORMATION: oligonucleotide

<400> SEQUENCE: 3
gcgaattcgg atccaccatg gaacaagccc cagaagac                    38

<210> SEQ ID NO 4
<211> LENGTH: 36
<212> TYPE: DNA
<213> ORGANISM: Artificial Sequence
<220> FEATURE:
<223> OTHER INFORMATION: oligonucleotide

<400> SEQUENCE: 4
gcgaattcgg atcctctagg atctactggc tccatt                      36
```

RETROVIRAL VECTORS

This is a continuation-in-part of U.S. application Ser. No. 09/915,169, filed on Jul. 25, 2001, now U.S. Pat. No. 6,669,936, which is a divisional application of U.S. application Ser. No. 09/224,014, filed on Dec. 28, 1998, now U.S. Pat. No. 6,312,682, which is a continuing application of PCT/GB97/02857, filed Oct. 17, 1997 and claiming priority to Great Britain Patent application Nos. 9621680.9, filed on Oct. 17, 1996, and 9624457.9, filed on Nov. 25, 1996. This application makes reference to U.S. application Ser. No. 10/408,456, filed on Apr. 7, 2003.

This invention relates to retroviral vector production systems and to retroviral vector particles produced by the systems. In particular, it relates to systems and vector particles from which certain retroviral auxiliary factors are absent. The invention also relates to uses of retroviral vectors, in particular for gene therapy.

Retroviral vectors have been the vehicle of choice for clinical gene transfer because of their efficacy, safety, and stable long-term gene expression. According to the United States National Institutes of Health RAC report issued in September 1996 (Ross et al., 1996), 76 out of 107 trials reviewed by the NIH were based on vector systems derived from the murine leukaemia virus (MLV).

One major drawback of these vectors is their inability to infect non-proliferating cells such as neurons, macrophages and haematopoeitic stem cells. These cells are important targets for gene therapy.

Human immunodeficiency virus type 1 (HIV-1) belongs to a sub-family within the retroviruses, the lentiviruses and in common with other members of this family HIV can infect quiescent cells. This makes lentiviruses attractive vectors for gene therapy.

The viral determinants for HIV-1 infection of non-dividing cells are thought to reside in the p17 matrix protein (MA) and vpr (Gallay et al., 1996). MA has karyophilic properties conferred by a conserved stretch of basic residues, which constitute a nuclear localization signal (NLS) (Bukrinsky et al., 1993). Vpr also contains a distinct NLS (Mahalingam et al., 1995). MA-NLS mutant viruses fail to replicate efficiently in macrophages in the absence of a functional vpr gene (Heinzinger et al., 1994). These data have been interpreted to mean that vpr as well as MA function as karyophilic determinants of HIV-1. In the absence of vpr the transduction efficiency of monocyte-derived macrophages decreases by over 50%, in the presence of functional MA. (Naldini et al., 1996).

Following work reported in Lever et al., 1989 which showed the sequences required for packaging of HIV-1, there has been much interest in the development of an HIV-1 based gene therapy vector. Transfer of foreign genes into a human T-cell line by a replication defective HIV-1 based vector was demonstrated by Poznanski et al (Poznansky et al., 1991). Other groups have designed HIV-1 based vectors that are tat-inducible (Buchschacher, Jr. and Panganiban, 1992) or that use heterologous promoters (Shimada et al., 1991). However, the viral titers obtained with these vectors was low (at most $10^3$ infectious particles per ml), and it was not clear whether the vector system could guarantee the production of helper virus-free vectors. More recently, new efforts to produce helper virus-free vectors have been based on three-plasmid cotransfections (Richardson et al., 1995). HIV vectors can be pseudotyped with Vesicular Stomatitis Virus glycoprotein (VSV-G) and these particles retain infectivity after concentration by ultracentrifugation (Akkina et al., 1996). Pseudotyping with VSV-G confers a broader host range and eliminates the chances of recombination to produce wild type HIV envelope. In vivo transduction of non-dividing neuronal cells has been demonstrated with VSV-G pseudotyping of HIV-1 in a three-plasmid cotransfection system (Naldini et al., 1996 and Naldini et al., 1996a).

HIV-1 contains nine genes, three of which: gag, pol and env are found in all retroviruses. These are the structural genes. The other six: vif, vpu, vpr, nef, tat and rev are referred to as auxiliary genes. Other retroviruses have different sets of auxiliary genes in their wild type genomes. Some of the auxiliary genes of other retroviruses are analogous to those of HIV-1, although they may not always have been given the same names in the literature. Analogous auxiliary genes have homology in their nucleotide sequences and perform the same or similar functions. HIV-2 and SIV strains generally contain env, vpr, vif, tat, and nef genes analogous to those of HIV-1. HIV-2 and some strains of SIV also contain vpx which, in some SIV strains lacking vpr,can be considered analogous to vpr. Lentiviruses other than HIV-1 also contain auxiliary genes which are not analogous to the HIV-1 auxiliary genes. Retrovirus auxiliary genes are reviewed for example by Tomonaga and Mikami (1996) and by Joag et al. in Fields Virology, Vol 2.

To date all vector systems based on HIV contain some or all of the HIV auxiliary genes. Rev acts as an RNA export protein and tat is a major transactivator of the proviral long terminal repeat (LTR). The auxiliary genes play a crucial role in viral replication and pathogenesis. The auxiliary genes have not been fully characterized nor their function defined.

However some of the auxiliary genes are thought to be involved in the pathogenesis of HIV-1. Tat has been implicated in the development of Kaposi's sarcoma (Barillari et al., 1993; Ensoli et al., 1990). HIV vpr has been shown to cause cell arrest and apoptosis and this has been proposed to be the cause of T-Cell dysfunction seen in AIDS patients (Jowett et al., 1995). Also extracellular Vpr present in peripheral blood has been suggested to contribute to tissue-specific pathologies associated with HIV infection since Vpr induces cell proliferation and differentiation (Levy et al, 1993 and Levy et al, 1995).

Since the roles of the auxiliary genes are not clear and they probably play a major role in pathogenesis their removal from HIV-1 vector production systems is desirable, provided that sufficiently high retrovirus vector titer and ability to transduce non-proliferating cells can be retained.

Naldini et al's data shows that the presence or absence of vpu has no effect on the vector particle titer. That is, a packaging system they used produced a titer of $4\times10^5$ when pseudotyped with VSV-G and this system was env and vpu negative. In another system which was only env negative they obtained the same titer (Naldini et al. 1996 and Naldini et al. 1996a). However, as already discussed another system of Naldini et al which was vpr negative as well as vpu negative gave a transduction efficiency which was decreased by 50% compared to a vpr positive system.

We have now discovered that leaving some or all of the auxiliary genes out of retrovirus vector production systems does not significantly compromise vector particle titers or the ability of the vector particles to transduce non-dividing cells.

The invention therefore provides in one aspect a retroviral vector production system for producing lentivirus-based, replication defective vector particles for gene therapy, said vector particles capable of infecting and transducing non-dividing mammalian target cells, which system comprises a set of nucleic acid sequences encoding the components of the vector, wherein one or more functional genes chosen from the HIV-1 auxiliary genes vpr, vif, tat and nef or from the analogous auxiliary genes of other lentiviruses, which auxiliary genes are normally present in the lentivirus on which the vector particles are based, is or are absent from the system. The functional vpu gene may also be absent, with the proviso that when the production system is for an HIV-1 based vector and vpr and vpu are both absent, so also is one of the other auxiliary genes.

In another aspect, the invention provides retroviral vector particles produced by a retroviral vector particle production system described herein.

In yet another aspect, the invention provides a DNA construct for use in a retroviral vector production system described herein, said DNA construct encoding a packagable RNA vector genome for a retroviral vector particle and operably linked to a promoter, wherein all of the functional retroviral auxiliary genes are absent from the construct, other than rev which is optionally present. The DNA construct may be provided as part of a set of DNA constructs also encoding some or all of the structural components of the vector particles.

In further aspects, the invention provides the use of retroviral vector particles as described herein, for gene therapy and in the preparation of a medicament for gene therapy; and a method of performing gene therapy on a target cell which method comprises infecting and transducing the target cell using a retroviral vector particle as described herein. The invention further provides transduced target cells resulting from these uses and methods. The invention thus provides a gene delivery system for use in medicine.

The expression "lentivirus-based" means that the vector particles are derived from a lentivirus. The genome of the vector particle comprises components from the lentivirus as a backbone. The vector particle as a whole contains essential vector components compatible with the RNA genome, including reverse transcription and integration systems. Usually these will include the gag and pol proteins derived from the lentivirus.

Being derived from a lentivirus, the retroviral vector particles are capable of infecting and transducing non-dividing cells. Thus, the vector particles are able to deliver a selected gene or genes such as therapeutically active genes, to the genome of a target cell. During the infection process, lentiviruses form a pre-integration complex in the target cell cytoplasm containing integrase, core proteins and proviral DNA. The complex is able to pass across the nuclear membrane of the target cell, by means of signal sequences in the proteins. Non-lentiviral retroviruses either lack the proteins or have the proteins but without the appropriate signal sequences.

Examples of lentiviruses are HIV-1 and HIV-2, SIV, FIV, BLV, EIAV, CEV and visna virus. Of these, HIV and SIV are presently best understood. However, a non-immunodeficiency virus may be preferred for use in gene therapy because the immunodeficiency viruses inevitably bring with them safety considerations and prejudices.

The absence of functional auxiliary genes from the retroviral vector production system means that those functional genes will also be absent from retroviral vector particles produced by the system. Also, any auxiliary proteins that would otherwise be encoded by those genes and incorporated into the vector particles, will be absent from the vector particles. In known retroviral vector production systems, the auxiliary genes may be present as part of the vector genome-encoding DNA, or together with the packaging components. The location of an auxiliary gene in a vector production system depends in part on its relationship with other retroviral components. For example, vif is often part of a gag-pol packaging cassette in a packaging cell. Thus, to remove a functional auxiliary gene for the purposes of the invention may involve its removal from the packaging components, or from the vector genome, or perhaps both.

To remove a functional auxiliary gene may not require removal of the gene in its entirety. Usually removal of part of the gene, or disruption of the gene in some other way will be sufficient. The absence of a functional auxiliary gene is understood herein to mean that the gene is not present in a form in which it is capable of encoding the functional auxiliary protein.

In a preferred system according to the invention, functional vpr and tat genes or analogous genes normally present in the lentivirus on which the vector particles are based are both absent. These two auxiliary genes are associated with characteristics of lentiviruses which are particularly undesirable for a gene therapy vector. However, other than by the proviso given above, the invention is not limited with regard to the combination of auxiliary genes that are absent. In a system according to the invention for producing HIV-1-based vector particles, any combination of three, or more preferably four, of the genes may be absent in their functional form. Most preferably, all five of the auxiliary genes vpr, vif, tat, nef, and vpu are absent in their functional form. Similarly, for systems concerned with other lentiviruses, it is most preferable that all of the auxiliary genes are absent in their functional form (except rev which is preferably present unless replaced by a system analogous to the rev/RRE system).

In order to ensure efficient export of RNA transcripts of the vector genome from the nucleus to the cytoplasm, it is preferable to include functional rev and rev response element (RRE) sequences in the vector genome, or to include alternative sequences in the genome which perform the same function as the rev/RRE system. For example, a functional analogue of the rev/RRE system is found in Mason Pfizer monkey virus. This is known as CTE and consists of an RRE-type sequence in the genome which is believed to interact with a factor in the infected cell. The cellular factor can be thought of as a rev analogue. Thus, CTE may be used as an alternative to the rev/RRE system.

As will be evident, in order to function as a vector the retroviral vector particles described herein will need to have a reverse transcription system (compatible reverse transcription and primer binding sites) and an integration system (compatible integrase and integration sites) allowing conversion to the provirus and integration of the double-stranded DNA into the target cell genome. Additionally, the vector genome will need to contain a packaging signal. These systems and signals will generally be derived from the lentivirus on which the vector is based. It will be evident that although the vector according to the invention is based on a lentivirus, the elements of the lentivirus incorporated into the vector may be genetically or otherwise altered versions of the elements in the wild type lentivirus. Alterations may be achieved by manipulating either the RNA genome or other components of the retroviral vector particle production system. For example, portions of the lentivirus genome not required for the vector can be excluded. Also, the vector production system can employ substitutes e.g. for the lentivirus env gene, to give the vector a different target cell range (this is known as pseudotyping).

A retroviral vector particle according to the invention carries one or more selected genes for delivery to a target cell. The selected genes are chosen according to the effect sought to be achieved. For gene therapy purposes there will be at least one therapeutically active gene encoding a gene product which is active against the condition it is desired to treat or prevent. Additionally there may be a selected gene which acts as a marker by encoding a detectable product. Therapeutic genes may encode for example an antisense RNA, a ribozyme, a transdominant negative mutant of a target protein, a toxin, a conditional toxin, an antigen that induces antibodies or helper T-cells or cytotoxic T-cells, a single chain antibody or a tumour suppressor protein.

Preferably the construction of the vector genome is such that in the DNA provirus, the therapeutic gene or genes is or are under transcriptional control of the 5' LTR but not otherwise operably linked to any other promoter from the vector. Thus, expression of the gene or genes is in a single transcription unit. Preferably also the 5' LTR is a modified lentivirus LTR for which the promoter function is not tat-dependent. This may be achieved by replacing the R and U3 lentivirus promoter functions by alternative promoter functions, which may be derived from another retrovirus or may be of non-retroviral origin. A strategy for this is described in Cannon et al 1996 and in the Examples.

It will be evident that the term "gene" is used loosely here, and includes any nucleic acid coding for the desired polypeptide or RNA. Usually, genes delivered by vectors according to the invention will be cDNAs.

Retroviral vector particles according to the invention will also be capable of infecting and transducing cells which are slowly-dividing, and which non-lentiviruses such as MLV would not be able to efficiently infect and transduce. Slowly-dividing cells divide once in about every three to four days. Mammalian non-dividing and slowly-dividing cells include brain cells, stem cells, terminally differentiated macrophages, lung epithelial cells and various other cell types. Also included are certain tumour cells. Although tumours contain rapidly dividing cells, some tumour cells especially those in the centre of the tumour, divide infrequently.

The DNA construct encoding the vector genome described herein is preferably linked to a high efficiency promoter such as the CMV promoter. Other high efficiency promoters are known. This gives rise to a high level of expression of the vector RNA by the retroviral vector production system.

Suitable host or producer cells for use in the retroviral vector production system according to the invention are well known in the art. Many retroviruses have already been split into replication defective genomes and packaging components. For those which have not the technology is available for doing so. The producer cell encodes the viral components not encoded by the vector genome such as the gag, pol and env proteins. The gag, pol and env genes may be introduced into the producer cell and stably integrated into the cell genome to give a packaging cell line. The retroviral vector genome is then introduced into the packaging cell line by transfection or transduction to create a stable cell line that has all of the DNA sequences required to produce a retroviral vector particle. Another approach is to introduce the different DNA sequences that are required to produce a retroviral vector particle e.g. the env coding sequence, the gag-pol coding sequence and the defective retroviral genome into the cell simultaneously by transient triple transfection. In a preferred system according to the invention, both the structural components and the vector genome will all be encoded by DNA stably integrated into a host cell genome.

Figure 1:
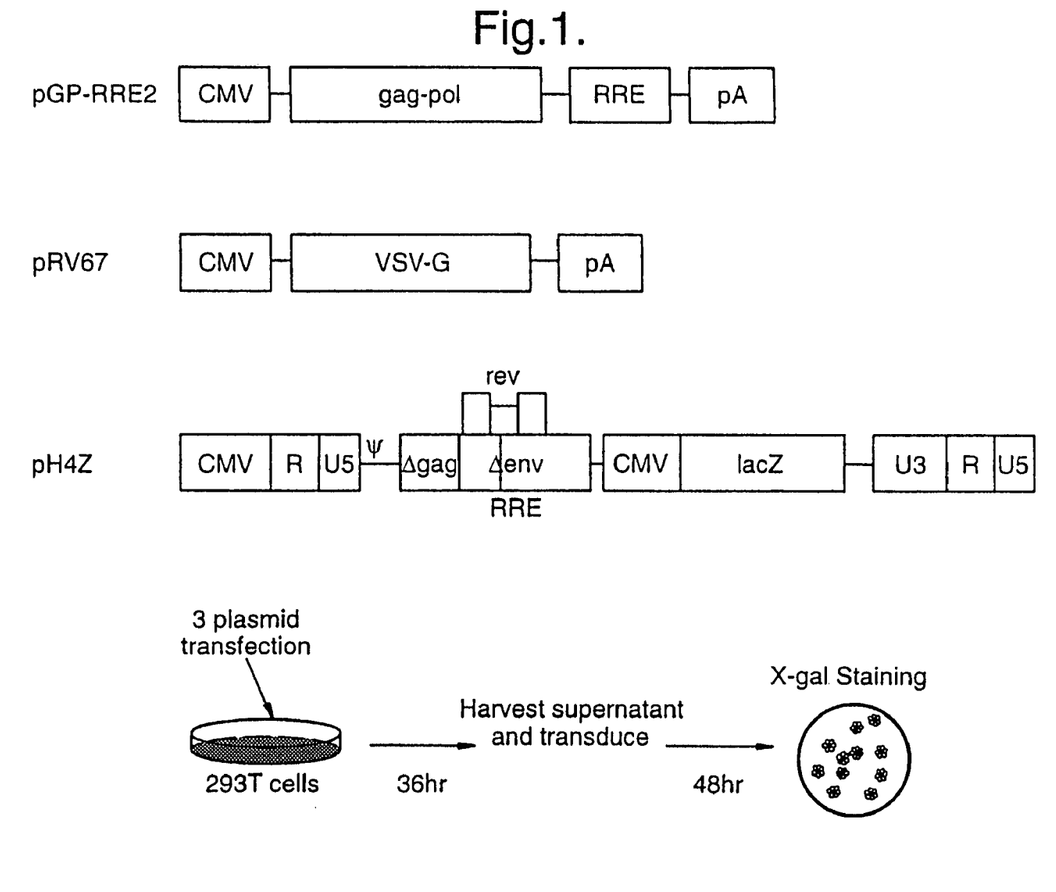
FIG. 1 shows a vector production system according to the invention, using a three-plasmid co-transfection of 293T cells.

To produce a safe HIV packaging system devoid of all unnecessary genes, we have developed a system which does not contain vpr, nef, tat, vif or vpu (FIG. 1.). The packaging components were placed on three separate plasmids and overlapping sequences were minimised ensuring no recombination and no helper virus production. This HIV vector has been shown to transduce aphidicolin treated non-dividing cells in the absence of vpr. Titers were obtained that are similar to the Naldini et al titers for systems which contain all the auxiliary genes (Naldini et al. 1996a).

This is the first minimal lentiviral vector system. The fact that high titers are observed with this system shows that the auxiliary genes (except rev) are redundant for the production of high titers and for the transduction of non-dividing cells. This is contrary to the assumption made by Naldini et al that the reason for the production of high titer virus stocks is due to the incorporation of accessory proteins (such as nef) into the viral particle (Naldini et al 1996).

The system may have additional advantages for HIV therapy. Replacing the HIV-1 LTR with a different promoter such as a constitutive HCMV promoter permits the use of anti-Tat molecules such as Tat transdominant mutants (Echetebu et al, 1994) or TAR decoys (Lisziewicz et al, 1993) as therapeutic agents as they will not affect vector production.

It will be evident that minimal lentiviral vectors as described herein, lacking all of the wild-type virus auxiliary genes, may also have applications as vaccines.

EXAMPLES

Materials and Methods

Plasmid Construction pGP-RRE1 is a pWI3 (Kim et al., 1989) derived gagpol vif expression plasmid. The RRE of pWI3 (Accession number: U26942) was inserted by blunt-ending the Sty I/Sty I fragment (7720–8050) into pBluescript KS+ Sma 1 cut creating pBSRRE. The Nar I/Eco RI fragment of pWI3 (637–5743) was inserted into pBSRRE cut with Cla I and Eco RI to create pBSGPRRE1. The Xho I/Not I fragment (containing gagpol and RRE) was inserted into the expression plasmid pCI-Neo to create pGR-RRE1. To remove the vif coding region, pBSGPRRE1 was cut with NdeI and SmaI, blunt-ended and was relegated to generate pBSG-PRRE2. The gagpol gene and RRE were inserted into pCI-neo in XhoI and NotI site to make pGP-RRE2.

The construction of pTIN406, pTIN408 and pTIN414 has been described (Cannon et al., 1996). The 5' LTR of pH3Z and pH4Z contain a CMV promoter at the U3 position and the HIV R and U5 regions. HIVdge was made from HIVgpt (Page et al., 1990) by blunt-ending the Cla I site (829) to create a frameshift mutation. HIVdge was cut with Bgl II and Pst I (473-1414) and inserted into pTIN406. pTIN406 has an LTR structure of CMV, R (HIV) and U5 (MLV). This created a hybrid LTR containing CMV, and R, U5 from HIV called pBS5'. To provide the plasmid with rev and RRE the Eco RI/Xho I fragment (5743-8897) was cut from HIVdge1.2 which is a HIVdge derivative containing a deletion from Nde I to Bgl II (6403-7621) and was inserted into pBS5' to create pBS5'R. The 3' LTR was provided by inserting the Not I/Xho I fragment of pBS3' into pBS5'R creating pH2. pBS3' was created by a three way ligation of the Xho I/Hind III fragment of pWI3, the Hind III/Kpn I fragment of pTIN408 into Bluescript KS+ (Xho I/KpnI). A CMV promoter was inserted into the unique Xho I site of pH2 from pSPCMV (Sal I/Xho I) making pH2CMV. pSPCMV was created by inserting pLNCX (Accession number: M28246) (Pst I/Hind III) into pSP72 (Promega). The β-galactosidase gene was inserted from PTIN414 into pSP72 (Xho I/Sph I) to make pSPlacZ. A Xho I/Sal I digest of pSPlacZ gave the β-galactosidase coding region which was inserted into pH2-CMV to give pH3Z. pH4Z was constructed to create tat-deficient vector. The first 50 bp of the tat-coding region was removed by replacing EcoRI (5743)I-SpeI fragment in pH3 with EcoRI (5881)-SpeI PCR product amplified using PCR primers DELT5 (5'-CGT-GAATTCGCCTAAAACTGCTTGTACCA-3') (SEQ ID NO:1) and DELT3 (5'-GAACTAATGACCCCGTAATTG-3') (SEQ ID NO:2) to create pH4. The Nsi I/Spe I fragment from pH4 was inserted into pH3Z to generate pH4Z.

A vpr expression plasmid was constructed by PCR amplification of the vpr coding region from pNL4.3 (Accession number: U26942) using the following primers: 5' primer GCGAATTCGGATCCACCATGGAACAAGC-CCCAGAAGAC (5563-5583) (SEQ ID NO:3) and 3' primer GCGAATTCGGATCCTCTAGGATCTACTG-GCTCCATT (5834-5853). (SEQ ID NO:4) This amplicon was cloned into pLIGATOR (R&D Systems). The expression plasmid pCI-vpr was made by inserting the Mlu I and Xho I fragment containing the vpr coding region into pCI-Neo (Promega).

pAC29.1 was cut by Bam HI to give the VSV-G coding region which was inserted into pSA91 (BgI II).

Cell Lines 293T (293ts/A1609) (DuBridge et al., 1987) cells were maintained in Dulbelco's modified Eagle's medium (GIBCO), HeLa cells and 208F cells in MEM (GIBCO), all of which containing 10% (v/v) fetal calf serum supplemented with antibiotics.

Production and Assays of Vectors

Retroviral vector stocks were produced according to our previously published protocol (Soneoka et al, 1995). Briefly, human kidney 293T ($1.5 \times 10^6$) cells were plated on 10-cm plates and transiently transfected with 15 mg of each plasmid (gag-pol and env expression plasmids together with a vector plasmid) by calcium phosphate DNA precipitation (Chen and Okayama, 1987). The culture supernatants were harvested 36 hours later, filtered through 0.45 mm and either used immediately or frozen at −70° C. Transduction was carried out by adding virus onto target cells for 2 hours, in the presence of 8 mg/ml polybrene followed by the addition of fresh media. 5-bromo-4-chloro-3-indolyly b-D-galactoside (X-Gal) was used to measure the expression of β-galactosidase 48 hours later, as previously described (Soneoka et al., 1995). Titers were obtained by counting the number of lac z (blue foci) forming units per ml (l.f.u./ml). G1/S phase arrested cultures were prepared by adding aphidicolin (5 mg/ml) 24 hours before infection and then daily throughout the experiment.

Results

HIV Vector Production

Figure 2:
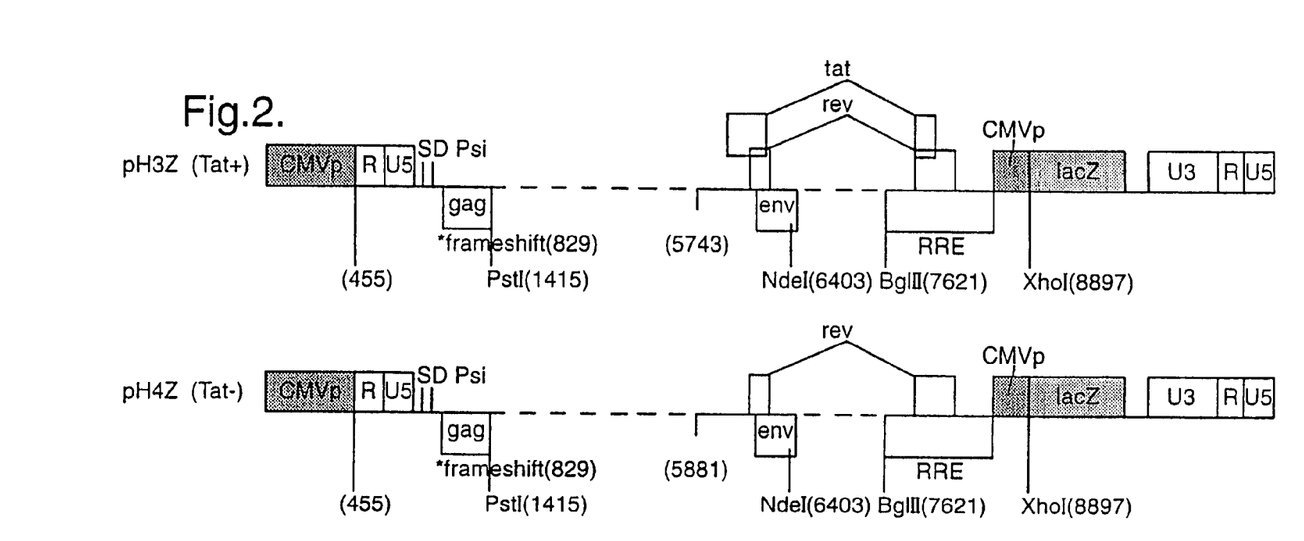
FIG. 2 shows HIV-based vector genomes for use in the invention.

H3Z (tat positive) and H4Z (tat negative) are HIV-1 based vectors designed to be produced by three plasmid co-transfection into 293T cells (FIG. 2). For efficient packaging by the HIV cores, the vectors contain the first 778 bases of gag but a frameshift mutation, introduced 40 bp from the ATG start codon, prevents the expression of gag proteins. RRE was included to boost packaging efficiency and rev is expressed from the vector to support the HIV mRNA export. The internal CMV promoter-driven β-galactosidase gene was inserted to serve as a reporter gene. For both the vector genomes transcription is driven by a CMV promoter which has been used to replace the 5' LTR U3. This makes the vector genome tat independent. Two HIV-1 gagpol constructs were made (FIG. 3); pGP-RRE1 (vif positive) and pGP-RRE2 (vif negative). Since the gagpol genes have been inserted into pCI-neo which is a CMV driven expression plasmid gagpol expression is tat independent pRV67, the VSV glycoprotein construct was used for the pseudotyping. By placing the different genes on different plasmids the probability of generating replication competent virus by recombination could be minimized.

Transduction Efficiency of the Vector

Replication defective retroviral particles were generated by transient co-transfection of human kidney 293T cells with the three plasmids described above and either used immediately or frozen at −70° C. The different vector constructs were used to produce virus. It was found that the minimal constructs (H4Z and pGP-RRE2) gave comparable titers to that of the vif, vpr, nef and tat positive viruses (Table 1).

When the minimal system was tested on various cell lines the titers differed (Table 2). The vectors yielded titers of $3.2 \times 10^5$ l.f.u./ml with polybrene treatment, $9.1 \times 10^4$ l.f.u./ml without polybrene treatment in 293T cells. Also the same vectors, without polybrene, yielded $9.6 \times 10^3$ l.f.u./ml and $8.3 \times 10^3$ l.f.u./ml in HeLa and 208F cells, respectively. These titers are comparable with those obtained by Naldini et al., 1996 (Naldini et al., 1996), which are the highest ones published so far.

Effect of vpr on the Transduction of Aphidicolin-Treated Cells

Figure 4A:
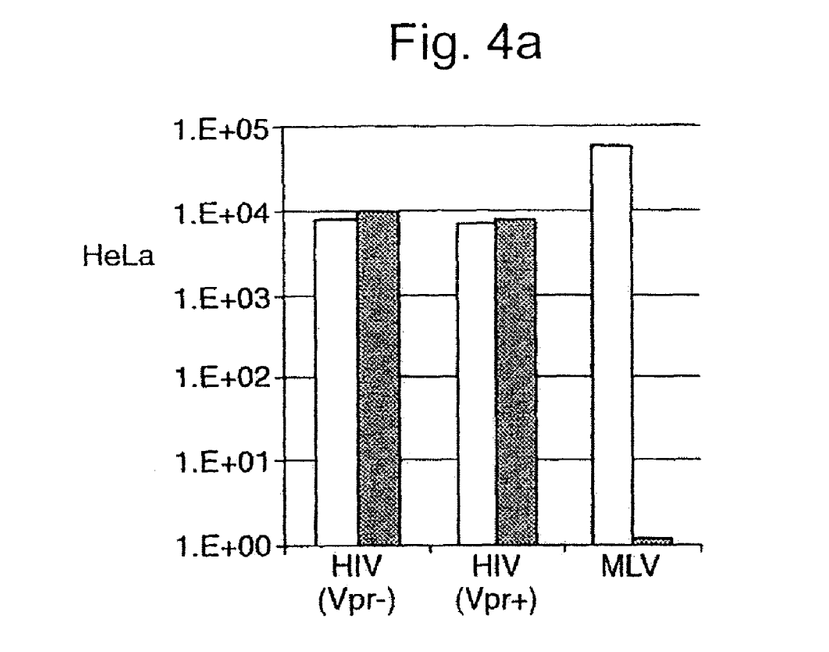
FIG. 4 shows transduction efficiencies for vectors according to the invention lacking the five auxiliary factors.
Figure 4B:
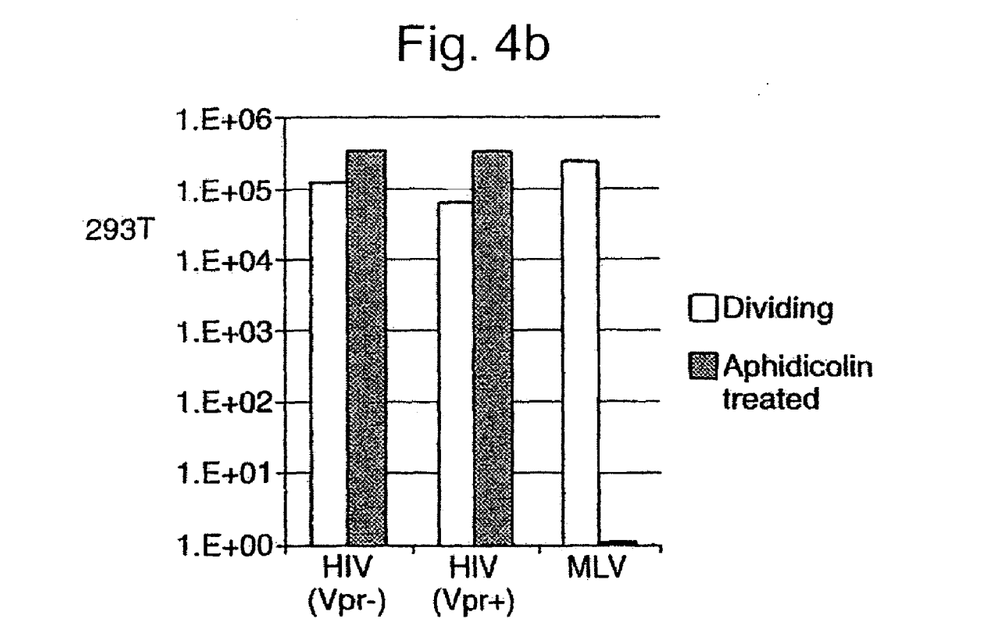

To test the effect of vpr on non-dividing cell transduction, vpr was included in the packaging system by co-transfection of pCI-vpr along with pH4Z, pGP-RRE2 and pRV67 plasmids. The transduction efficiencies of the viral particles generated were assayed on growing and growth-arrested 293T cells and HeLa cells (FIG. 4). MLV-derived packaging and transducing vectors (Soneoka, 1995) served as controls. HeLa cells and 293T cells were growth-arrested at G1/S phase by aphidicolin treatment. The minimal HIV vector H4Z was as efficient at transducing G1/S-arrested as proliferating HeLa and 293T cells, whereas the MLV-based vector was only 0.002% as effective.

Vpr-deficient H4Z could transduce the growth-arrested cells as efficiently as vpr-containing vector, suggesting that HIV-1 MA is sufficient for providing the vector with the ability to transduce non-dividing cells.

Conclusion

We have set up an HIV-1 based vector production system, which does not contain vpr, vpu, nef, vif and tat based on a three-plasmid co-transfection method. This vector can transduce proliferating cells with a titer of up to $3.2 \times 10^5$ l.f.u./ml, which is comparable to other MLV-based vectors and can easily be increased by concentration using ultracentrifugation (data not shown). No helper virus has been detected (data not shown).

This minimal vector has been demonstrated to transduce growth-arrested HeLa cells and 293T cells as efficiently as vpr, vif, nef and tat containing vectors. Therefore it can be concluded that only rev is required for the production of high titer HIV based vectors and that these vectors can transduce non-dividing cells.

This is the first report of the construction of a high titer minimal lentiviral vector that can transduce non-dividing cells. The removal of five out of the six auxiliary genes (except rev) and the minimal sequence overlap between the plasmids makes this system the safest one to date for the production of HIV-vectors for gene therapy.

Figure Legends

FIG. 2. HIV vector genomes. The numbers indicate the coordinates from HXB2. HCMV promoter (−597 to −1). HIV sequences (455 to 1415; 5743 (H3Z) or 5881 (H4Z) to 6403; 7621 to 8897; 8897 to 9720) from HXB2. HCMV promoter as an internal promoter (900 bp). Cloning site (XhoI). Backbone; pBluescriptKS+.

Figure 3:
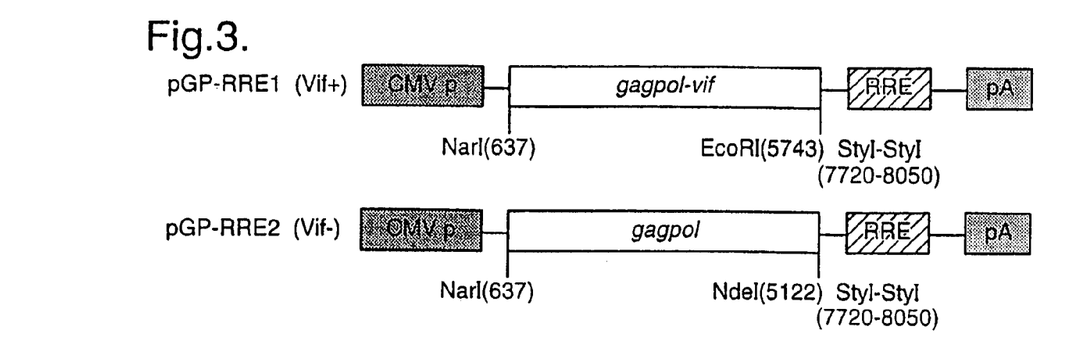
FIG. 3 shows HIV-1 gag-pol gene expression plasmids for use in the invention.

FIG. 3. HIV-1 gag-pol gene expression plasmids. HIV-1 gagpol coding region and RRE was cloned into pCI-neo (PROMEGA) at XhoI and NotI site.

FIG. 4. Transduction of non-dividing cells. Transduction efficiencies of the H4Z vectors were measured by X-gal staining and are shown in Y-axis as l.f.u./ml. G1/S phase arrested cells were prepared by treating the cells with aphidicolin (5 μg/ml).

REFERENCES

Akkina, R. K., Walton, R. M., Chen, M. L., Li, Q. X., Planelles, V., and Chen, I. S. (1996). J. Virol. 70, 2581–2585.
Barillari, G., Gendelman, R., Gallo, R. C., and Ensoli, B. (1993). Proc. Natl. Acad. Sci. U.S.A. 90, 7941–7945.
Buchschacher, G. L., Jr. and Panganiban, A. T. (1992). J. Virol. 66, 2731–2739.
Bukrinsky, M. I., Haggerty, S., Dempsey, M. P., Sharova, N., Adzhubel, A., Spitz, L., Lewis, P., Goldfarb, D., Emerman, M., and Stevenson, M. (1993). Nature 365, 666–669.
Cannon, P. M., Kim, N., Kingsman, S. M., and Kingsman, A. J. (1996). J. Virol. 70, 8234–8240.
Chen, C. and Okayama, H. (1987). Mol. Cell Biol. 7, 2745–2752.
Echetebu, C. O., H. Rhim, C. H. Herrmann and A. P. Rice (1994), J. Acquired Immune Defic. Syndrome. 7, 655–664.
Ensoli, B., Barillari, G., Salahuddin, S. Z., Gallo, R. C., and Wong Staal, F. (1990). Nature 345, 84–86.
Gallay, P., Stitt, V., Mundy, C., Oettinger, M., and Trono, D. (1996). J. Virol. 70, 1027–1032.
Heinzinger, N. K., Bukinsky, M. I., Haggerty, S. A., Ragland, A. M., Kewalramani, V., Lee, M. A., Gendelman, H. E., Ratner, L., Stevenson, M., and Emerman, M. (1994). Proc. Natl. Acad. Sci. U.S.A. 91, 7311–7315.
Joag, S. V., Stephens, E. B. and Narayan, O. in Fields Virology, Vol 2, 1970–1982 (Lippincott-Raven Publishers).
Jowett, J. B., Planelles, V., Poon, B., Shah, N. P., Chen, M. L., and Chen, I. S. (1995). J. Virol. 69, 6304–6313.
Kim, S. Y., Byrn, R., Groopman, J., and Baltimore, D. (1989). J. Virol. 63, 3708–3713.
Lever, A., Gottlinger, H., Haseltine, W., and Sodroski, J. (1989). J. Virol. 63, 4085–4087.
Levy, D. N., L. S. Fernandes, W. V. Williams, and D. B. Weiner (1993), Cell, 72, 541–50.
Levy, D. N., Y. Refae;; and D. B. Weiner (1995), J. Virol., 69, 1243–52.
Lisziewicz, J., D. Sun, J. Smythe, P. Lusso, F. Lori, A. Louie, P. Markham, J. Rossi, M. Reitz and R. C. Gallo (1993), Proc. Natl. Acad. Sci, USA, 90, 8000–4.
Mahalingam, S., Collman, R. G., Patel, M., Monken, C. E., and Srinivasan, A. (1995). Virology 212, 331–339.
Naldini, L., Blomer, U., Gallay, P., Ory, D., Mulligan, R., Gage, F. H., Verma, I. M., and Trono, D. (1996). Science 272, 263–267.
Naldini, L., Blomer, U., Gage, F. H., Trono, D., and Verma, I. M. (1996). Proc. Natl. Acad. Sci. U.S.A. 93, 11382–11388.
Page, K. A., Landau, N. R., and Littman, D. R. (1990). J. Virol. 64, 5270–5276.
Poznansky, M., Lever, A., Bergeron, L., Haseltine, W., and Sodroski, J. (1991). J. Virol. 65, 532–536.
Richardson, J. H., Kaye, J. F., Child, L. A., and Lever, A. M. (1995). J. Gen. Virol. 76, 691–696.
Ross, G., Erickson, R., Knorr, D., Motulsky, A. G., Parkman, R., Samulski, J., Straus, S. E., and Smith, B. R. (1996). Hum. Gene Ther. 7, 1781–1790.
Shimada, T., Fujii, H., Mitsuya, H., and Nienhuis, A. W. (1991). J. Clin. Invest. 88, 1043–1047.
Tomonaga, K. and Mikami, T. (1996). J. General Virol. 77, 1611–1621.

TABLE 1

Effects of accessory gene expression on vector titer.

| Accessory genes | | | | Plasmids | | | | Titer (l.f.u./ml)[a] |
|---|---|---|---|---|---|---|---|---|
| Tat | Vif | Nef | Vpr | Vector | Gagpol | Nef | Vpr | |
| + | + | − | + | pH3Z | pGP-RRE1 | | pCI-Vpr | 2.2 × 10⁵ |
| + | + | + | − | pH3Z | pGP-RRE1 | pC-Nef | | 2.5 × 10⁵ |
| + | + | − | − | pH3Z | pGP-RRE1 | | | 4.0 × 10⁵ |
| + | − | − | − | pH3Z | pGP-RRE2 | | | 3.7 × 10⁵ |
| − | − | − | − | pH4Z | pGP-RRE2 | | | 4.6 × 10⁵ |

[a]Transduction efficiency was measured in 293T cells by counting the number of blue colonies following X-gal staining 48 hours after transduction and were indicated as lacZ colony forming unit per ml virus stock (l.f.u./ml).

TABLE 2

Transduction efficiency of the minimal H4Z vector on various cell lines.

| | | Titer (l.f.u./ml)[a] | |
|---|---|---|---|
| Cell line | | Without polybrene | With polybrene |
| 293T | Human kidney | 9.1 × 10⁴ | 3.2 × 10⁵ |
| HeLa | Human epithelium | 9.6 × 10³ | N.D. |
| 208f | Rat fibroblast | 8.3 × 10³ | N.D. |

[a]Transduction efficiency was measured by counting the number of blue colonies following X-gal staining 48 hours after transduction and were indicated as lacZ colony forming unit per ml virus stock (l.f.u./ml).

The invention claimed is:

1. A lentivirus-based retroviral vector production system for producing a replication defective retroviral vector, wherein the retroviral vector production system comprises an expression construct encoding a lentivirus-based retroviral vector genome, and a separate expression construct or constructs encoding gag, pol, and an envelope protein, wherein the retroviral vector production system lacks nucleic acid sequences encoding functional tat, and wherein the retroviral vector production system is capable of producing a replication defective retroviral vector.

2. the retroviral production system according to claim 1, wherein the nucleic acid sequences encoding tat are absent or disrupted in the vector system.

3. The retroviral vector production system according to claim 1, further comprising a nucleic acid sequence encoding functionally active rev or RRE-type sequences.

4. The retroviral vector production system according to claim 3, wherein at least one RRE-type sequence is a constitutive transport element (CTE).

5. The retroviral vector production system according to claim 4, wherein the CTE is Mason Pfizer monkey virus CTE.

6. The retroviral vector production system according to claim 1, further comprising at least one nucleotide sequence of interest (NOI).

7. The retroviral vector production system according to claim 6, wherein the at least one NOI encodes a therapeutic protein or gene product of interest.

8. A method for producing a replication defective retroviral vector comprising at least one NOI, comprising contacting the retroviral vector production system of claim 6 with a cell, thereby producing the replication defective retroviral vector.

9. An isolated cell comprising the retroviral vector production system of claim 1.

10. A composition comprising the retroviral vector production system of claim 1 and a carrier.

11. The retroviral vector production system according to claim 1, wherein the system comprises separate DNA constructs which encode: (i) the lentivirus-based retroviral vector genome, (ii) gag and pol proteins, and (iii) an envelope protein.

12. The retroviral vector production system according to claim 1, wherein the lentivirus-based retroviral vector genome comprises an operable promoter.

13. The retroviral vector production system according to claim 12, wherein the promoter is a non-retroviral promoter.

14. The retroviral vector production system according to claim 1, wherein the envelope protein is VSV-G.

15. The retroviral vector production system according to claim 1, wherein the retroviral vector production system is based on HIV-1.

16. A set of separate DNA constructs comprising a DNA construct which encodes a replication-defective lentivirus-based retroviral vector genome, a DNA construct which encodes gag and pol proteins, and a DNA construct which encodes an envelope protein, wherein the set of DNA constructs lacks nucleic acid sequences encoding functional Tat.

17. The set of separate DNA constructs according to claim 16, further comprising a DNA construct which encodes a functionally active rev or RRE-type sequences.

18. The set of separate DNA constructs according to claim 16, wherein the DNA construct encoding the lentivirus-based retroviral vector genome further comprises at least one NOI.

19. A method for producing a replication defective retroviral vector, comprising expressing in a cell the retroviral vector production system according to claim 1, thereby producing the replication defective retroviral vector.

* * * * *